United States Patent [19]

Igaue et al.

[11] Patent Number: 5,342,341
[45] Date of Patent: Aug. 30, 1994

[54] DISPOSABLE GARMENTS AND METHOD FOR ATTACHMENT OF ELASTIC MEMBERS AROUND LEG-HOLES THEREOF

[75] Inventors: Takamitsu Igaue, Kawanoe; Hironori Nomura; Hirofumi Ohnishi, both of Iyomishima; Yoshinori Matsura, Kanonji; Tohru Sasaki, Kawanoe; Taiji Shimakawa, Kanonji; Hiroki Yamamoto, Kagawa, all of Japan

[73] Assignee: Uni-Charm Corporation, Ehime, Japan

[21] Appl. No.: 756,226

[22] Filed: Sep. 9, 1991

[30] Foreign Application Priority Data

Sep. 13, 1990 [JP] Japan .................................. 2-243417
Apr. 17, 1991 [JP] Japan .................................. 3-113986

[51] Int. Cl.$^5$ .............................................. A61F 13/15
[52] U.S. Cl. .................................................. 604/385.2
[58] Field of Search .............. 604/358, 385.1, 385.2, 604/370; 2/400-402

[56] References Cited

U.S. PATENT DOCUMENTS

| | | | |
|---|---|---|---|
| 4,300,562 | 11/1981 | Pieniak | 604/370 X |
| 4,425,128 | 1/1984 | Motomura | 604/384 X |
| 4,430,086 | 2/1984 | Repke | 604/385 |
| 4,661,102 | 4/1987 | Shikata et al. | 604/385.2 |
| 4,726,807 | 2/1988 | Young et al. | 604/385.2 |
| 5,069,678 | 12/1991 | Yamamoto et al. | 604/358 X |

FOREIGN PATENT DOCUMENTS

| | | |
|---|---|---|
| 0048101 | 3/1982 | European Pat. Off. . |
| 0405575 | 6/1990 | European Pat. Off. . |
| 0421473 | 4/1991 | European Pat. Off. . |
| 2091985 | 8/1982 | United Kingdom ............. 2/401 |
| 2236663A | 4/1991 | United Kingdom . |

Primary Examiner—Randall L. Green
Assistant Examiner—Mary Beth O. Jones
Attorney, Agent, or Firm—Fred Philpitt

[57] ABSTRACT

Here are disclosed disposable garments such as diaper and training pants and a method for attachment of threadlike continuous elastic members (each comprising a plurality of threadlike elastic elements) around leg-holes thereof so that the elastic members are progressively widened from their longitudinally opposite ends toward their longitudinally middle portions, respectively.

The threadlike continuous elastic members 4A, 4B thus attached to the article around the respective leg-holes each comprises rubber threads 4a,4b, 4c. The traverse arrangement support these rubber threads in parallel to one another and forcibly guide them in sine curves with respect to the continuous web 7 so that the portions 4A$_1$, 4B$_1$ of the elastic members 4A, 4B to be bonded to the continuous web are bonded thereto. Then, the non-bonded portions 4A$_2$, 4B$_2$ of the elastic members are cut together with the web 7 along boundaries of the individual articles and thereupon contract under their own stretch stresses.

2 Claims, 6 Drawing Sheets

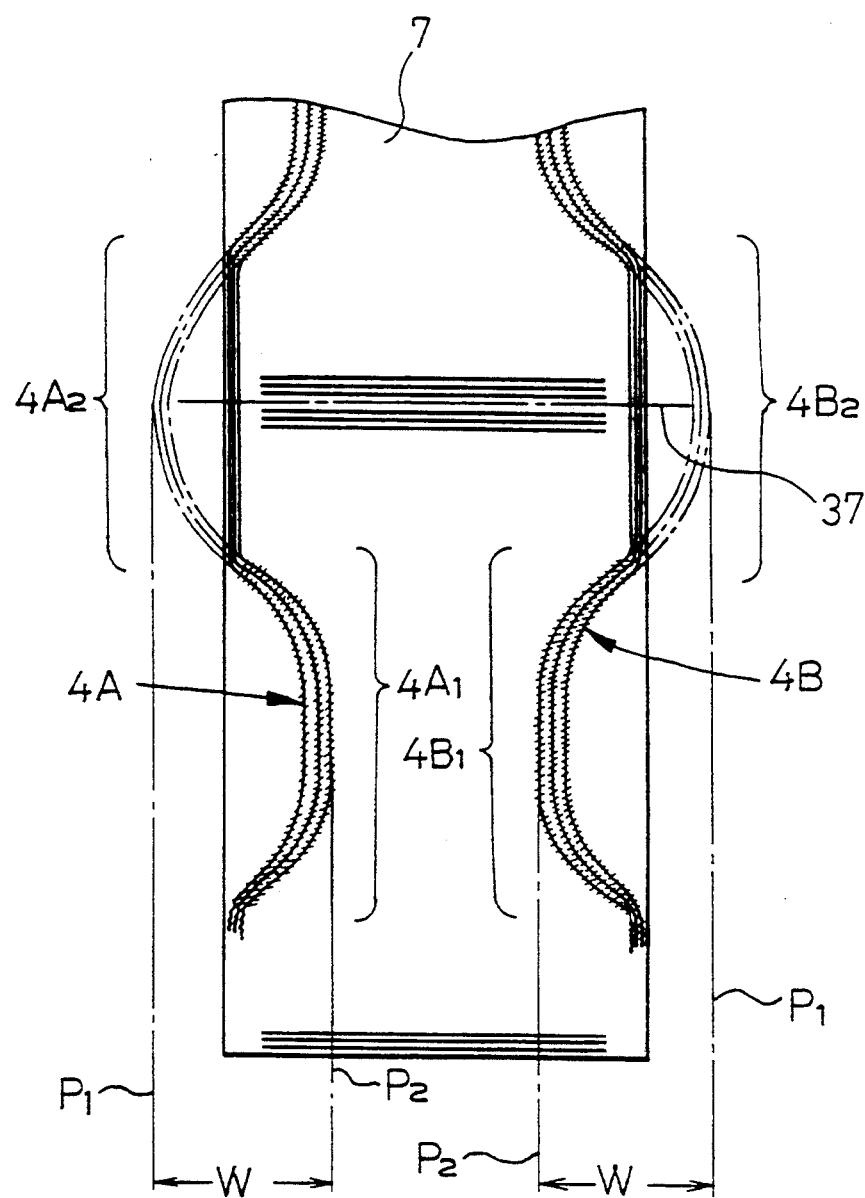

DISPOSABLE GARMENTS AND METHOD FOR ATTACHMENT OF ELASTIC MEMBERS AROUND LEG-HOLES THEREOF

BACKGROUND OF THE INVENTION

The present invention relates to disposable garments such as diaper, incontinence pants and training pants and a method for attachment of elastic members around leg-holes thereof.

Such garments are usually provided around the leg-holes with the elastic members and, in general, the elastic members are fixedly bonded to at least one of the top- and backsheet.

With the garment put on wearer's skin, excretion leak often occurs along approximately lower halves of the respective leg-holes and therefore it is preferred to arrange the elastic members extensively over said approximately lower half of each leg-hole so that the garment may tightly fit the wearer's skin particularly over this area.

However, the garments of such type having conventionally been proposed and commonly put to practical use as well as the methods or apparatuses for making them have taken no account of the extensive arrangement of the elastic members extensively over said approximately lower half of the leg-holes and have suggested neither method nor apparatus to achieve such arrangement.

Accordingly, it is a principal object of the present invention to provide disposable garments and a method for attachment of the elastic members around the respective leg-holes thereof so that said elastic members may be arranged more extensively over the approximately lower halves than over the upper halves of the respective leg-holes.

SUMMARY OF THE INVENTION

Product:

Disposable garments are provided around circular-arc-shaped leg-holes respectively formed on opposite sides of a crotch section defined front and rear sections of top- and backsheets with elastic members each comprising a plurality of elastic elements. Said plurality of elastic elements for each of said leg-holes are so arranged that said elastic elements are most widely spaced from one another at longitudinally reduced from said middle portions to longitudinally opposite ends thereof.

Method:

Threadlike continuous elastic members each comprising a plurality of elastic elements are supported, in their stretched condition, by groups of parallelly spaced guides provided on respective traverse means adjacent forward ends thereof and said traverse means are reciprocated transversely of continuous web being continuously fed as material of a top- or backsheet in each garment so that said threadlike continuous elastic members may be bonded to said continuous web with said elastic elements being curved in parallel to one another.

To bond said threadlike continuous elastic members to said continuous web, said continuous web may be previously applied with adhesive or said threadlike continuous elastic members may be applied with adhesive as said threadlike continuous elastic members are guided and arranged by said traverse means onto said continuous web.

The remainder components of the garments are laminated on said continuous web to which said threadlike continuous elastic members have been bonded. Then said continuous web is transversely cut together with the threadlike continuous elastic members in zones where said threadlike continuous elastic members have not been bonded to said continuous web and thereby the non-bonded portions of said threadlike continuous elastic members are caused to contract under their own stretch stresses.

According to the present method, the respective groups of parallelly spaced guides of said traverse means support said threadlike continuous elastic members each comprising a plurality of elastic elements in their stretched condition and are reciprocated transversely of said continuous web so as to guide said threadlike continuous elastic members onto said continuous web in curves of a given wave frequency. Consequently, said threadlike continuous elastic members are bonded to said continuous web with the respective plurality of elastic elements being curved in parallel to one another and more widely spaced from one another at the longitudinally middle portions than at the longitudinally opposite ends (of the adhesive zones in the individual garments). These curved portions of said threadlike continuous elastic members that have been bonded to said continuous web function as the threadlike elastic members around the respective leg-holes in the finished garments.

BRIEF DESCRIPTION OF THE DRAWINGS

FIG. 6 is a plan view illustrating a partial variation in the arrangement of the threadlike continuous elastic members illustrated by FIG. 4.

PREFERRED EMBODIMENT OF THE INVENTION

Figure 1:
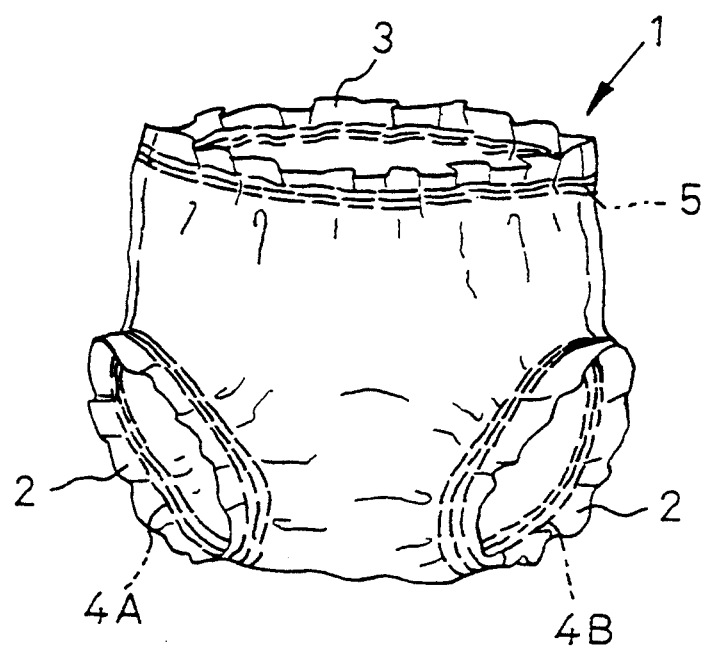
FIG. 1 is a perspective view of a garment to be made by an embodiment of the method according to the present invention.

FIG. 1 is a perspective view showing by way of example a garment made by a method of the present invention. The garment 1 has a pair of leg-holes 2 and a waist-hole 3 provided with threadlike elastic members 4A; 4B and 5, respectively.

Figure 2:
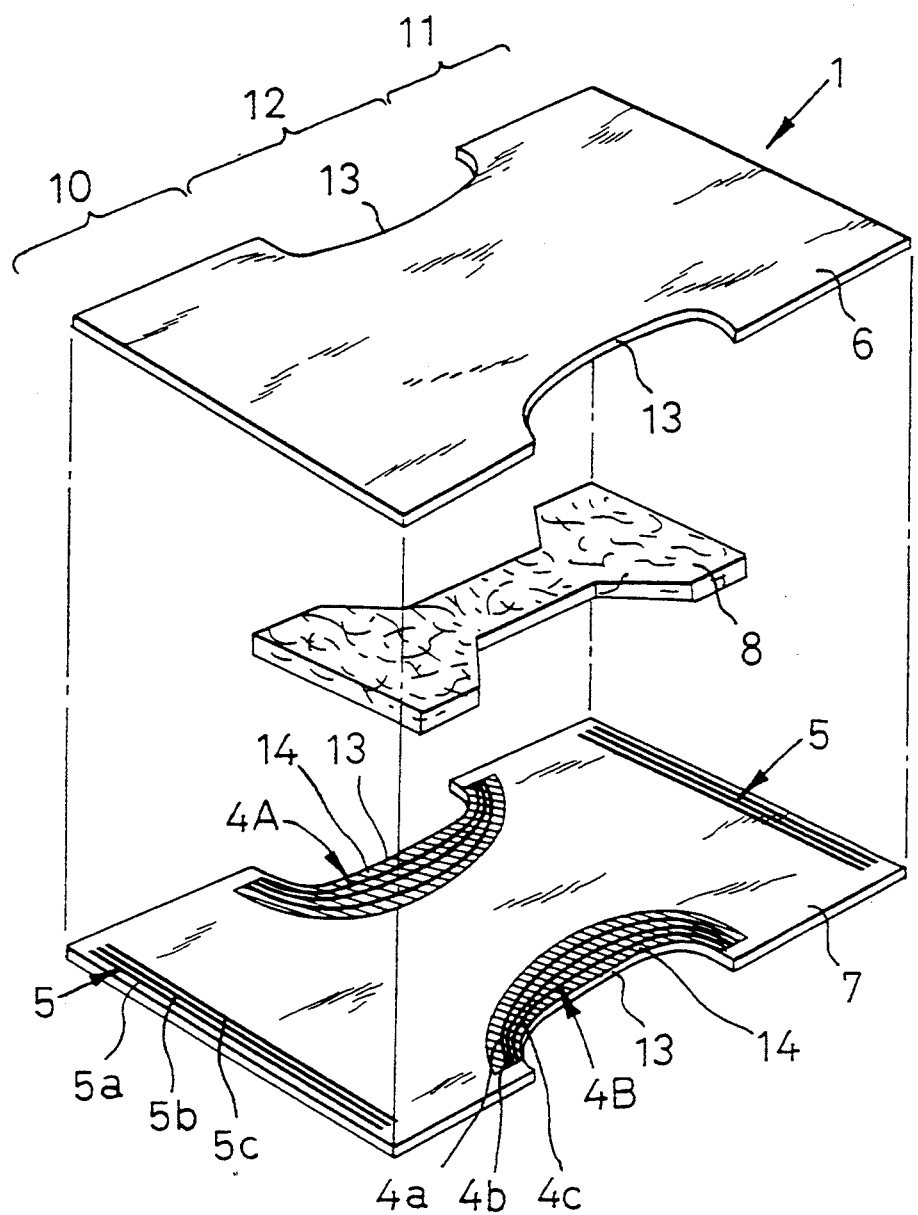
FIG. 2 is an exploded perspective view of said garment.

FIG. 2 is an exploded perspective view of the garment 1. The garment 1 comprises a topsheet 6 made of liquid-permeable nonwoven fabric which is stretchable both in length and width, a backsheet 7 made of liquid-impermeable nonwoven fabric which is stretchable both in length and width, a mat- or sheet-like liquid absorbent core 8 substantially made of fluffy pulp and said threadlike elastic members 4A; 4B and 5 arranged around the leg-holes and the waist-hole, respectively. A crotch section 12 extending between front and rear sections 10, 11 of said top- and backsheets is formed along opposite side edges with concavely curved notches 13 corresponding to said leg-holes 2. Though not shown, it is also possible to employ the backsheet 7 comprising liquid-permeable nonwoven fabric being stretchable both in length and width and liquid-impermeable plastic or rubber film being stretchable both in length and width, which has been intermittently bonded to the inner side of said liquid-permeable nonwoven fabric with adhesive. The arrangement as has been mentioned just above not only allows the backsheet 7 to achieve perfect prevention of liquid excretion from permeating it, but also, when at least the outer periphery of said film is intermittently bonded to the topsheet 6 with adhesive, improves stretchability of the top- and backsheets 6, 7 as primary materials of the garments and, in consequence, enhances a stretch stress characteristic, resulting in further improving a fitness of the garment 1 to a wearer's body.

Each of the threadlike elastic members 4A and 4B provided around the respective leg-holes comprises a plurality of natural or synthetic rubber threads 4a, 4b, 4c extending in parallel to one another with spacings being gradually reduced from longitudinally middle portions (corresponding to the crotch section) toward longitudinally opposite ends and with their stretch stress being gradually weakened from the longitudinally middle portions toward the longitudinally opposite ends, and is bonded to the backsheet 7 along an associated curved adhesive zone 14 extending along the associated concavely curved notch 13 and having been applied with adhesive. Similarly, the threadlike elastic member 5 comprises a plurality of natural or synthetic rubber threads 5a and 5b bonded to the backsheet 7 along an adhesive zone (not shown) defined by adhesive applied to the backsheet or with adhesive applied to these rubber threads themselves.

Figure 3:
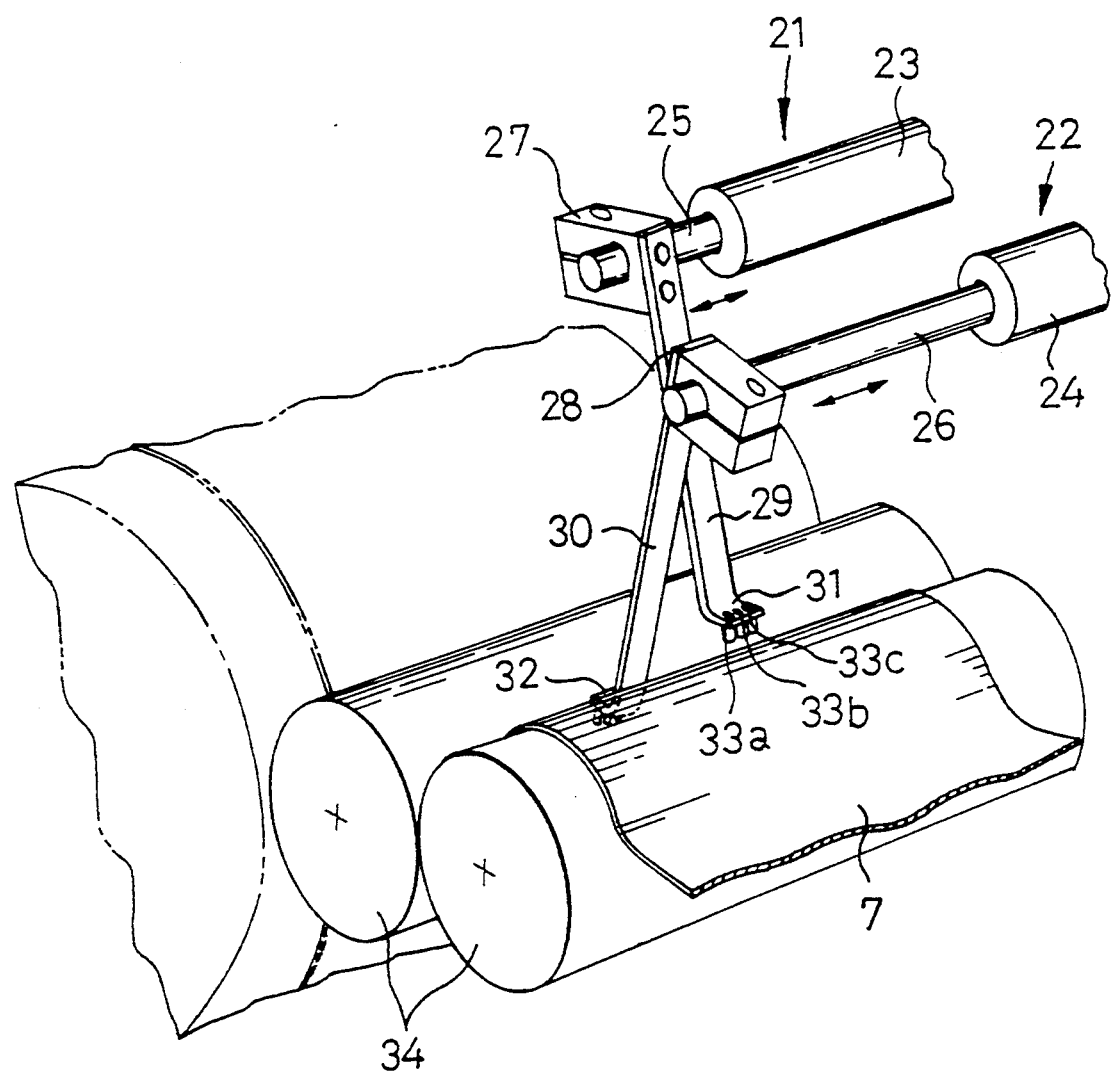
FIG. 3 is a schematic perspective view of traverse means used to perform a procedure for attachment of threadlike continuous elastic members to a continuous web.

FIG. 3 is a schematic perspective view illustrating traverse means used to attach the threadlike continuous elastic members to the continuous web 7 as material of the individual backsheets in the manner as has been described above and FIG. 4 is a plan view illustrating how to attach the threadlike continuous elastic members to the continuous web by utilizing said traverse means. The apparatus to perform this method is well known except the traverse means as shown, and this method can be performed also by utilizing the disposable diaper making apparatus of prior art, for example, the apparatus disclosed by the applicant in EP 0 405 575 A1.

Referring to FIG. 3, the traverse means 21, 22 comprise support cylinders 23, 24 extending adjacent to and in parallel to a pair of squeeze rollers 34, 34, slidable levers 25, 26 inserted into said support cylinders 23, 24, respectively, support blocks 27, 28 secured to forward ends of said slidable levers 25, 26, respectively, and guide levers 29, 30 depending from said support blocks 27, 28, respectively. Each of said guide levers 29, 30, is provided on its curved lower end 31, 32 with a plurality of small cylindrical guides 33a, 33b, 33c. These guides 33a, 33b, 33c are spaced from one another in a direction in which the associated guide lever 29, 30 moves. The curved ends 31, 32 are closely adjacent peripheral surfaces of the respective squeeze rollers 34, 34. The slidable levers 25, 26 are controlled by traverse cam mechanisms (not shown) linked to rear ends of the respective slidable levers 25, 26 in a manner as will be described later.

Figure 4:
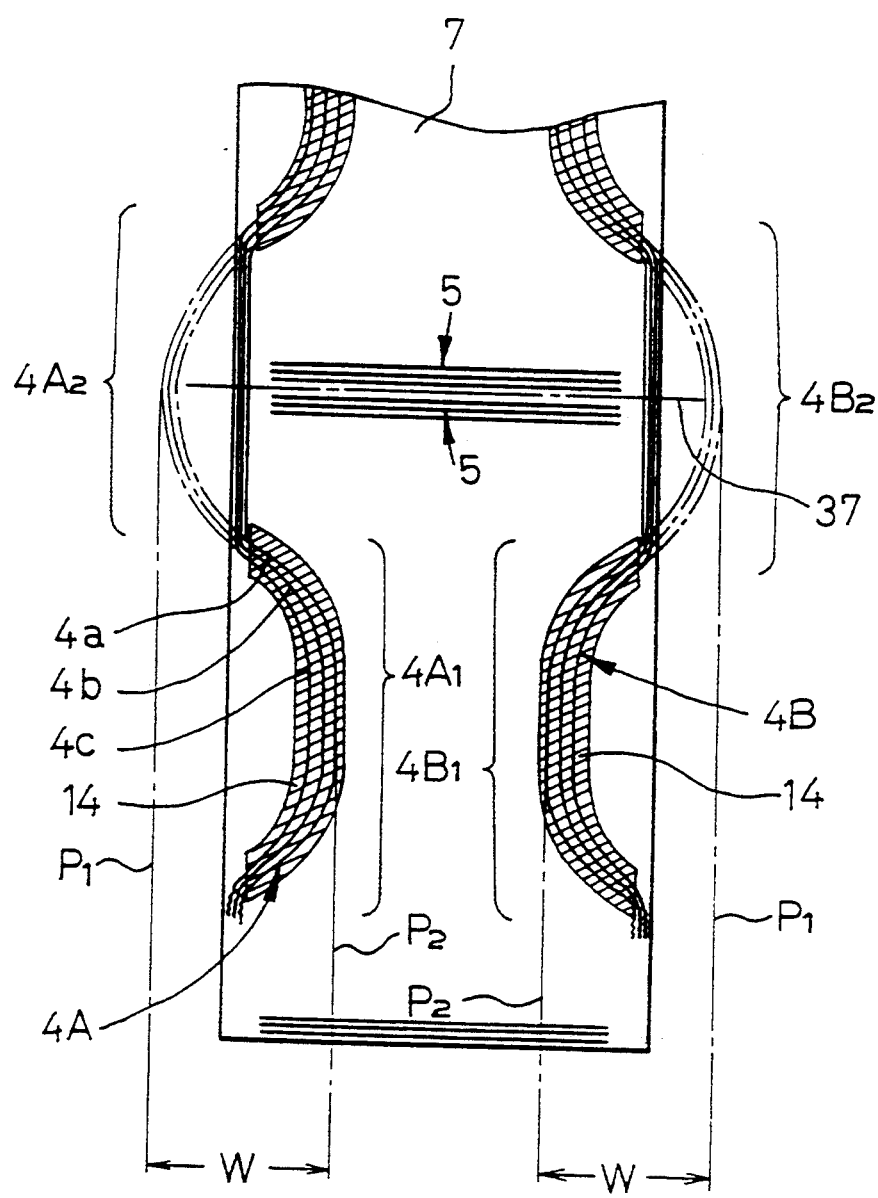
FIG. 4 is a schematic plan view illustrating how the threadlike continuous elastic members are attached to the continuous web utilizing said traverse means.

Referring to FIG. 4, the continuous web 7 is intermittently applied with adhesive at given intervals along opposite side edges so as to form successive adhesive zones 14 concavely curved with respect to the associated side edges as said continuous web 7 is longitudinally moved at a given velocity. Meanwhile, the rubber threads 4a, 4b, 4c constituting the respective threadlike elastic members 4A, 4B are made run through the respective guides 33a, 33b, 33c of said traverse means 21, 22 while said rubber threads 4a, 4b, 4c are stretched at a given percentage of elongation. From this state, the guide levers 29, 30 are reciprocated transversely across the respective side edges of the continuous web 7 so that the rubber threads 4a, 4b, 4c of the respective groups (i.e., the threadlike elastic members 4A, 4B) describe sine curve like curves tracing the respective adhesive zones 14 symmetrically to each other.

The threadlike continuous elastic members 4A, 4B are moved from a first position $P_1$ to a second position $P_2$ and from the second position $P_2$ to the first position $P_1$, respectively, by a width W, wherein their percentage of elongation are slightly increased and their stretch stresses are correspondingly increased during movement from the first position $P_1$ to the second position $P_2$. More specifically, the threadlike continuous elastic members 4A, 4B being stretched at a given percentage of elongation and linearly running along the length of the continuous web 7 are forcibly directed by said guide livers 29, 30 transversely of the continuous web 7 and a resistance of the respective elastic members 4A, 4B against such forcible change of direction causes these elastic members 4A, 4B to be stretched as they are moved from the first position $P_1$ to the second position $P_2$. It should be understood, in this regard, that a degree of such elongation depends upon a velocity at which the threadlike continuous elastic members 4A, 4B are moved longitudinally of the continuous web 7 and a velocity at which said guide levers 29, 30 are moved transversely of said continuous web 7.

The rubber threads 4a, 4b, 4c of the respective groups moving in parallel to the length of the continuous web 7 are forcibly directed by said guide levers 29, 30 transversely of said continuous web 7 and the spacings of these rubber threads are enlarged as they are moved from the first position $P_1$ to the second position $P_2$. More specifically, such effect is achieved by an arrangement that the previously mentioned cylindrical guides 33a, 33b, 33c are spaced in parallel from one another transversely of the direction in which the continuous web 7 is moved, on one hand, and said traverse means 21, 22 are controlled so as to increase curvature radii of the respective rubber threads progressively from longitudinally opposite ends to longitudinally middle portions of the respective curved adhesive zones 14, on the other hand.

In this manner, portions $4A_1$, $4B_1$, of the threadlike continuous elastic members 4A, 4B extending just on the respective adhesive zones 14 are pressed thereagainst by said squeeze rollers 34, 34 and thereby bonded to the respective adhesive zones 14. Portions $4A_2$, $4B_2$ of the threadlike continuous elastic members 4A, 4b extending out of said adhesive zones 14 contract under their own stretch stress into linear condition but still maintaining a certain stretch stress. Such maintenance of stretch stresses is essential for the reason as will be described later and can be controlled by the elongation percentage of the threadlike continuous elastic members 4A, 4B and the curvature radii of said non-bonded portions $4A_2$, $4B_2$.

Figure 5:
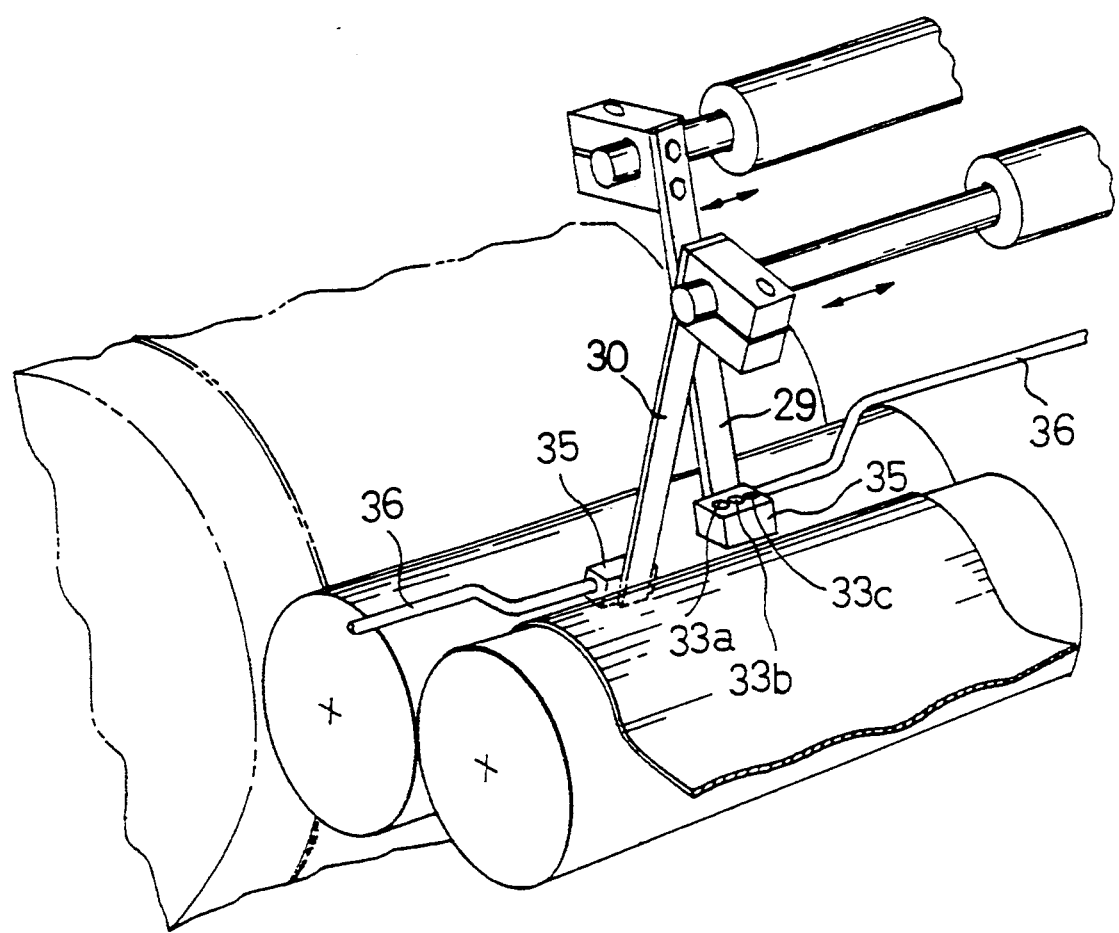
FIG. 5 is a perspective view showing a partial variation of said traverse means shown by FIG. 3.

FIGS. 5 and 6 are perspective and plan views, respectively, illustrating partial variations in the arrangement of said traverse means and said threadlike continuous elastic members illustrated by FIGS. 3 and 4, respectively. In these variants illustrated by FIGS. 5 and 6, the threadlike continuous elastic members 4A, 4B are intermittently and directly applied with adhesive.

Referring to FIG. 5, the guide levers 29, 30 are provided on lower ends thereof with adhesive applicator means 35, 35 which are in fluid communication with the respective guides 33a, 33b, 33c. These means 35 are supplied from separately provided adhesive supply devices (not shown) with adhesive under a predetermined pressure through respective flexible hoses 36, 36 so that the threadlike continuous elastic members 4A, 4B are intermittently in the longitudinal direction thereof applied with adhesive. Consequently, as shown by FIG. 6, portions applied with adhesive, i.e., the portions $4A_1$, $4B_1$ of the threadlike continuous elastic members 4A, 4B to be bonded to the continuous web 7 are provided (portions of the respective rubber threads 4a, 4b, 4c having short lines crossing them are continuously applied with adhesive, respectively). When it is desired to apply the individual rubber threads with adhesive separately, the applicator means (nozzles) disclosed by the present applicant in U.S. Pat. No. 4,626,305.

The method proposed herein by the present invention utilizes the traverse means to forcibly curve the threadlike continuous elastic members with respect to the continuous web and bond them in the curved condition to said continuous web. Accordingly, the continuous elastic members used in the present invention must be made of threadlike elements. For example, if the continuous elastic members comprising relative wide elements are used in the method of the present invention, the continuous elastic members tend to be twisted and peel off from the continuous web during the bonding operation due to unreliable bonding. Cross-section of each threadlike continuous elastic member suitable for the method of the invention may be circular (inclusive of oval), rectangular or of other indeterminate shapes, but it is undesirable that a ratio of the maximum cross-sectional dimension and the minimum cross-sectional dimension is significantly large.

Attachment of the threadlike elastic member 5 to the continuous web 7 is achieved by utilizing the apparatus and the method of well known art for making disposable diaper. It is also possible to use a single, relatively wide tape-like element instead of the threadlike elastic member 5 comprising the plural rubber threads.

Though not shown, the previously formed core 8 is placed on the continuous web 7 between the portions $4A_1$, $4B_1$ of the threadlike continuous elastic members 4A, 4B opposed to each other transversely of the continuous web 7, then another continuous web (not shown) as material of the topsheet 6 is fed onto this assembly and laminated thereon or on at least the continuous web 7 with interposition of adhesive layer, and finally portions of these continuous webs extending outside the portions $4A_1$, $4B_1$ are cut off to form a continuous laminate.

Said continuous laminate is transversely cut along lines connecting the middle points of the respective opposed non-bonded portions $4A_2$, $4B_2$ of the threadlike continuous elastic members 4A, 4B (along the line designated by reference numeral 37 in FIGS. 4 and 6) to obtain blanks of the individual garments. When the continuous laminate is cut into the blanks of the individual garments, the non-bonded portions $4A_2$, $4B_2$ of the threadlike continuous elastic members 4A, 4B snap back under their own residual stretch stresses.

Each garment blank is folded along a longitudinally middle line and longitudinally opposite ends are heat-sealed together to a finished article 1 as illustrated by FIG. 1.

It is also possible without departure from the scope of the present invention to attach the threadlike continuous elastic members to the continuous web used as the topsheet, instead of the continuous web used as the backsheet.

As will be understood from the foregoing description, the present invention allows the threadlike continuous elastic members each comprising a plurality of threadlike elastic elements to be easily attached around the respective leg-holes of each garment in the optimal arrangement. More specifically, said plurality of threadlike elastic elements can be easily bonded to the component of the individual garment so that the respective elastic elements are curved in parallel to one another and the spacings thereof are progressively widened from their longitudinally opposite ends toward their longitudinally middle portions (corresponding to the crotch section).

What is claimed is:

1. In a disposable garment which is adapted to contain liquid excretions comprising a topsheet (6), a backsheet (7), an absorbent core (8), a waist opening, two leg openings each leg opening having a top and a bottom, and elastic members surrounding each of said leg openings, the improvement comprising that said elastic members consist of a plurality of arcuate threadlike elastic elements (4a, 4b, 4c) that are disposed in a side-by-side spaced apart relationship with the spacings between adjacent elastic elements (4a, 4b, 4c) being gradually reduced from the bottom of each leg opening to the top of each leg opening and the stretch stress of said elastic elements (4a, 4b, 4c) being gradually reduced from the bottom of each leg opening to the top of each leg opening.

2. In a disposable garment which is adapted to contain liquid excretions comprising a topsheet (6), a backsheet (7), an absorbent core (8), a waist opening, two leg openings each leg opening having a top and a bottom, and elastic members surrounding said leg openings, the improvement comprising that said elastic members consist of a plurality of threadlike elastic elements (4a, 4b, 4c) that are each in the shape of an arc and which are disposed in a side-by-side spaced apart relationship with the spacings between adjacent arcuate elastic elements (4a, 4b, 4c) being gradually reduced from the bottom of each leg opening to the top of each leg opening.

* * * * *